(12) United States Patent
Hsieh et al.

(10) Patent No.: US 7,515,678 B2
(45) Date of Patent: Apr. 7, 2009

(54) METHOD AND SYSTEM FOR PERFORMING CT IMAGE RECONSTRUCTION WITH MOTION ARTIFACT CORRECTION

(75) Inventors: Jiang Hsieh, Brookfield, WI (US); Darin Robert Okerlund, Muskego, WI (US); Mark Edward Woodford, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 114 days.

(21) Appl. No.: 11/286,899

(22) Filed: Nov. 23, 2005

(65) Prior Publication Data

US 2007/0116171 A1 May 24, 2007

(51) Int. Cl.
- H05G 1/60 (2006.01)
- H05G 1/64 (2006.01)
- H05G 1/58 (2006.01)

(52) U.S. Cl. .............. 378/8; 378/19; 378/115; 378/116; 250/370.09; 600/428

(58) Field of Classification Search ............ 378/8, 378/15, 16, 19, 20, 95, 108, 109, 110, 115, 378/116; 600/428
See application file for complete search history.

(56) References Cited

U.S. PATENT DOCUMENTS

| 4,442,489 | A | * | 4/1984 | Wagner | 378/19 |
| 4,550,371 | A | * | 10/1985 | Glover et al. | 378/4 |
| 5,400,378 | A | * | 3/1995 | Toth | 378/16 |
| 5,832,051 | A | * | 11/1998 | Lutz | 378/8 |
| 6,173,033 | B1 | * | 1/2001 | Klingenbeck-Regn et al. | 378/20 |
| 6,243,438 | B1 | * | 6/2001 | Nahaliel et al. | 378/19 |
| 6,246,742 | B1 | * | 6/2001 | Besson et al. | 378/8 |
| 6,256,368 | B1 | * | 7/2001 | Hsieh et al. | 378/8 |
| 6,275,560 | B1 | * | 8/2001 | Blake et al. | 378/8 |
| 6,298,111 | B1 | * | 10/2001 | Ozaki | 378/8 |
| 6,385,278 | B1 | * | 5/2002 | Hsieh | 378/8 |
| 6,445,761 | B1 | * | 9/2002 | Miyazaki et al. | 378/8 |
| 6,501,828 | B1 | * | 12/2002 | Popescu | 378/150 |
| 6,507,639 | B1 | * | 1/2003 | Popescu | 378/108 |
| 6,560,309 | B1 | * | 5/2003 | Becker et al. | 378/8 |
| 6,700,948 | B2 | * | 3/2004 | Hoffman | 378/19 |
| 6,765,983 | B2 | * | 7/2004 | Yan et al. | 378/8 |
| 6,810,102 | B2 | * | 10/2004 | Hsieh et al. | 378/4 |
| 7,113,569 | B2 | * | 9/2006 | Okumura et al. | 378/150 |

FOREIGN PATENT DOCUMENTS

WO  WO 98/36690  *  8/1998

* cited by examiner

*Primary Examiner*—Allen C. Ho
(74) *Attorney, Agent, or Firm*—The Small Patent Law Group; Dean D. Smith

(57) ABSTRACT

In one embodiment, a method is provided for performing computed tomography (CT) imaging. The method includes obtaining EKG gating information from an object and obtaining attenuation measurements from the object utilizing a detector that is rotated in a scan plane around the object. The method further includes performing a first reconstruction based on a first portion of the attenuation measurements that are collected by a first region of the detector, where the first reconstruction is performed independent of the EKG gating information to obtain a first reconstruction data set. A second reconstruction is performed based on a second port of the attenuation measurements that are collected by a second region of the detector, where the second reconstruction is performed based on the EKG gating information to obtain a second reconstruction data set.

26 Claims, 9 Drawing Sheets

METHOD AND SYSTEM FOR PERFORMING CT IMAGE RECONSTRUCTION WITH MOTION ARTIFACT CORRECTION

RELATED APPLICATION

The present application relates to Utility Application with application Ser. No. 11/286,924 filed Nov. 23, 2005, titled "METHOD AND SYSTEM FOR PERFORMING CT IMAGE RECONSTRUCTION WITH MOTION ARTIFACT CORRECTION", the complete subject matter of which is hereby expressly incorporated in its entirety.

BACKGROUND OF THE INVENTION

The invention relates generally to methods and apparatus for CT imaging, and more particularly to methods and apparatus for performing computed tomography (CT) imaging utilizing first and second reconstructions of at least partially common attenuation measurements and EKG gating information.

In certain known computed tomography (CT) imaging systems, an x-ray source transmits x-ray beams through an object of interest. The x-ray beams pass through the object being imaged, such as a patient. The beams, after being attenuated by the object, impinge upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. Attenuation measurements from the detectors are acquired separately for each detector element and collectively define a projection data set or transmission profile.

The x-ray source and the detector array are rotated on a gantry within an imaging plane around the object to be imaged such that the angle at which the x-ray beam intersects the object constantly changes. A group of x-ray attenuation measurements, e.g., projection data set, from the detector array at one gantry angle is referred to as a "view". A "scan" of the object comprises a set of views made at different gantry angles, or view angles, during one revolution of the x-ray source and detector. The projection data sets are processed to construct images that correspond to two-dimensional slices taken through the object at various angles. One exemplary method for forming an image from a projection data set is referred to as filtered back projection technique.

The medical community has become increasingly concerned with reducing the x-ray dose to a patient during a CT examination. In Europe, for example, strict guidelines have been instituted to prevent potential danger of exposing patients and operators to excessive x-ray radiation. New uses of CT imaging have increased the interest in limiting x-ray exposure of patients. In cardiac screening CT, for example, asymptomatic patients undergo routine CT scans to detect calcification in coronary arteries. However, in certain instances, to provide cardiac screening, conventional CT systems and reconstruction techniques may perform more scans of the patient than performed by scans of non-cardiac anatomy. For example, additional scans may be taken to obtain more projection data sets to accurately reconstruct the heart. The additional scans are used to obtain sufficient information at various points in the cardiac cycle to support a reconstruction that is compensate for motion artifacts. Also, even if the radiation within an individual cardiac examination remains the same as in noncardiac examinations, as CT examinations are used for more types of screening, the patient will receive more radiation (e.g., a virtual colonoscopy, upper and lower GI examinations, vascular examinations and the like).

Further, the size of detectors used in CT systems continues to increase in order to obtain information regarding larger and larger regions of interest. In the example of cardiac screening, the region surrounding the heart (e.g. the lungs and other anatomy) is also of interest as well as the heart itself. CT systems with large detectors, when used in more frequent scans or longer scans, potentially increase the overall dosage to the patient.

It is desirable to provide a more efficient CT system and reconstruction techniques that reconstruct moving objects, such as the heart and reconstruct large field of views.

Also, certain conventional CT systems actively manage the tube current utilized to control the x-ray source. For example, conventional CT systems may modulate the tube current based on the view angle, where the current is increased when the x-ray source and detector are located laterally on opposites sides of a patient. The tube current may then be decreased as the x-ray source and detector rotate to locations above and below the patient. Another form of tube current modulation is ECG gated modulation, where the tube current is increased and decreased based on the cardiac cycle. In ECG gated modulation, the tube current may be increased to a peak level at the diastole point in the cardiac cycle and may be decreased to a minimum level at the systole point in the cardiac cycle. A third form of tube current modulation is Z-profile modulation, where the tube current is modulated in the Z-direction based on a Z-axis attenuation profile. The Z-axis attenuation profile may be predetermined based on general patient population statistics. The Z-axis attenuation profile may be determined during a scout scan of a patient. During the scout scan, the patient is scanned with a very low dose and attenuation measurements are obtained along the length of the patient. The attenuation measurements are used to form an attenuation profile of the patient in the Z-direction.

It is desirable to provide improved tube current modulation techniques that better manage the application of x-ray energy relative to particular organs of interest. It is also desirable to combine the use of multiple reconstruction techniques, each technique of which exhibits certain advantages depending upon characteristics of the scan data (e.g., noise, scan data overlap, gating information, etc.).

BRIEF SUMMARY OF THE INVENTION

In one embodiment, a method is provided for performing computed tomography (CT) imaging. The method includes obtaining EKG gating information from an object and obtaining attenuation measurements from the object utilizing a detector that is rotated in a scan plane around the object. The method further includes performing a first reconstruction based on a first portion of the attenuation measurements that are collected by a first region of the detector, where the first reconstruction is performed independent of the EKG gating information to obtain a first reconstruction data set. A second reconstruction is performed based on a second portion of the attenuation measurements that are collected by a second region of the detector, where the second reconstruction is performed based on the EKG gating information to obtain a second reconstruction data set.

Optionally, the detector may have a nonuniform cross-section in a Z-direction, where the Z-direction corresponds to a path along which the object is moved through the scan plane. Optionally, the first and second regions of the detector may partially differ and partially overlap. Optionally, the method may further include combining the reconstruction data sets by combining a central portion of the second reconstruction data set and a peripheral portion of the first reconstruction data set.

In accordance with one embodiment, the second reconstruction utilizes the EKG gating information to select certain projection data sets for reconstruction and retaining only a central portion of the second reconstruction data set that is corrected for motion artifacts, while the first reconstruction does not utilize the central portion of the first reconstruction data set and does not utilize the EKG gating information to correct for motion artifacts. Optionally, an outer portion of the second reconstruction data set may be based on estimated attenuation measurements, while an outer portion of the first reconstruction data set is based on actual attenuation measurements, not estimated attenuation measurements.

In accordance with an alternative embodiment, a system is provided for performing computed tomography (CT) imaging. The system includes EKG inputs, configured to receive EKG gating information from an object, and an x-ray source and detectors configured to obtain attenuation measurements from the object while the detector rotates in a scan plane around the object. The system includes a reconstruction module that performs first and second reconstructions based on first and second portions of the attenuation measurements, respectively, to obtain first and second reconstruction data sets. The first portion of the attenuation measurements is collected by a first region of the detector independent of the EKG gating information, while the second portion of the attenuation measurements is collected by a second region of the detector and is based on the EKG gating information.

Optionally, the detector may have a nonuniform cross-section in a Z-direction, where the Z-direction corresponds to a path along which the object is moved through the scan plane. Optionally, the first and second regions may partially differ and partially overlap. Optionally, the reconstruction module may further combine the reconstruction data sets by combining a central portion of the second reconstruction data set and a peripheral portion of the first reconstruction data set.

In accordance with one embodiment, the reconstruction module utilizes the EKG gating information to select certain projection data sets for reconstruction and retaining only a central portion of the second reconstruction data set that is corrected for motion artifacts, but does not utilize the central portion of the first reconstruction data set and does not correct the first reconstruction data set for motion artifacts. Optionally, the reconstruction module may based an outer portion of the second reconstruction data on estimated attenuation measurements, while an outer portion of the first reconstruction data set is based on actual attenuation measurements, not estimated attenuation measurements.

DETAILED DESCRIPTION OF THE INVENTION

Figure 1:
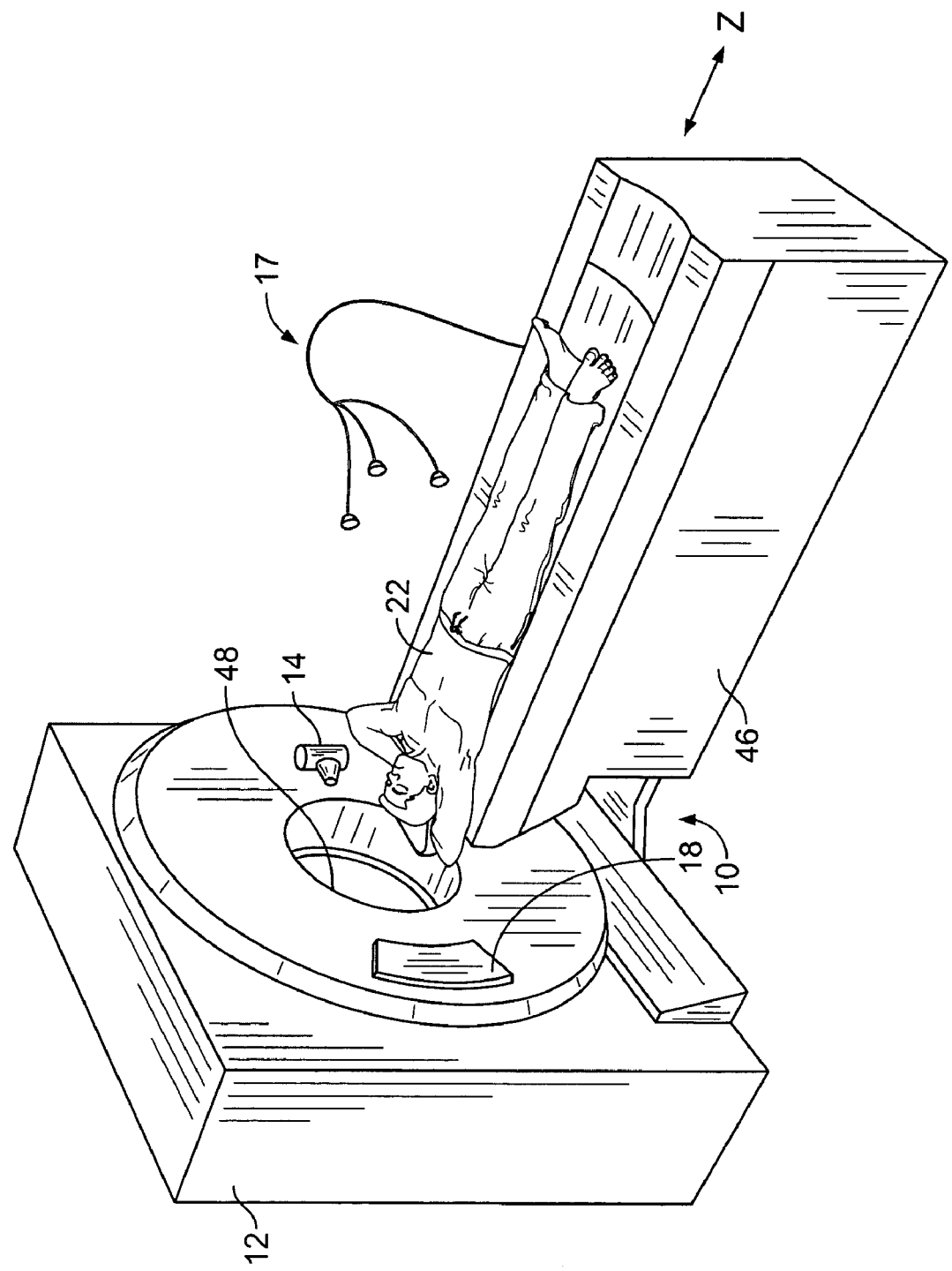
FIG. 1 illustrates a CT imaging system operated in accordance with an embodiment of the present invention.
Figure 2:
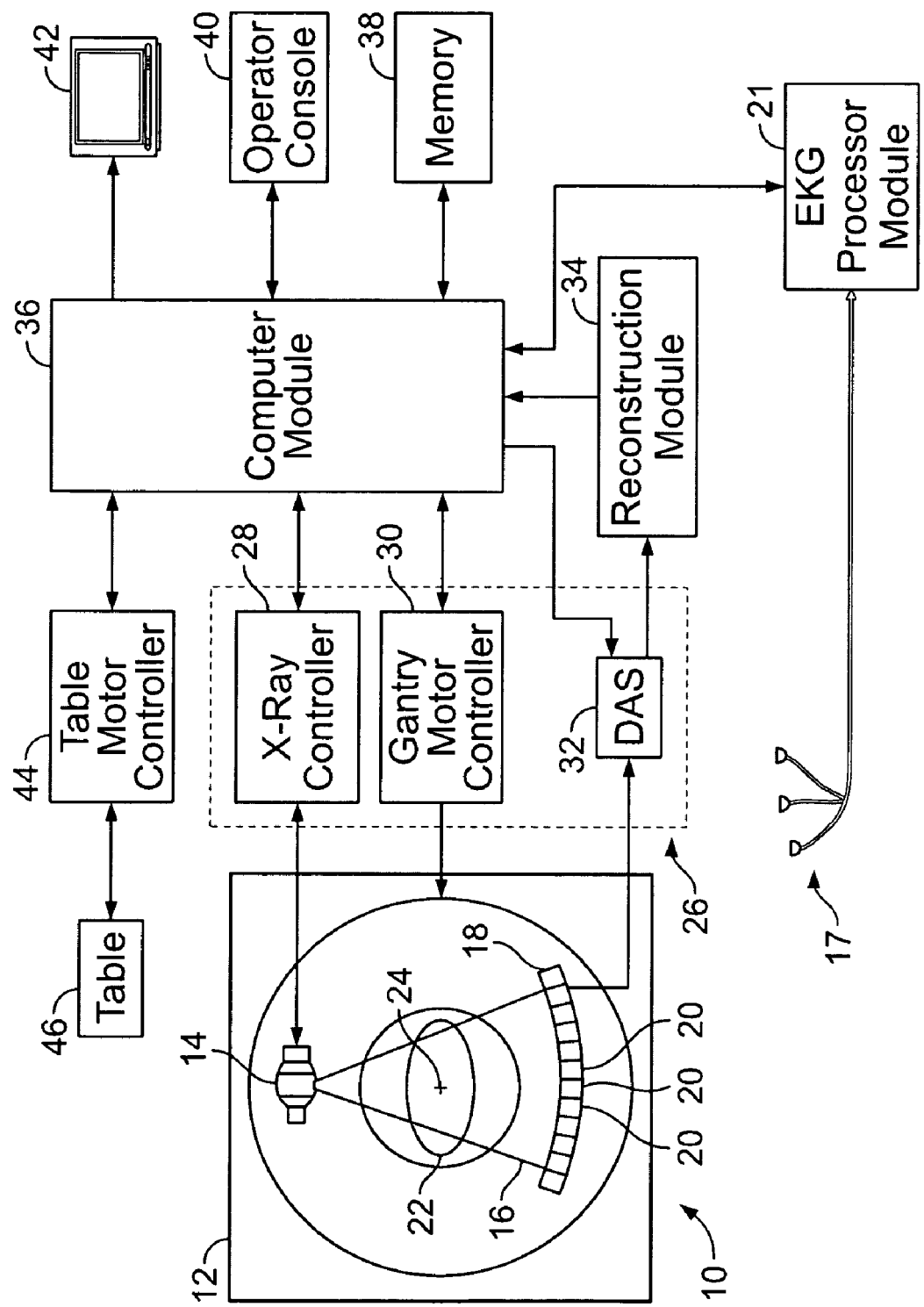
FIG. 2 illustrates a block diagram of the system illustrated in FIG. 1.

Referring to FIGS. 1 and 2, a computed tomograph (CT) imaging system 10 is shown that includes a gantry 12 for a CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through object 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. The DAS 32 outputs projection data sets including attenuation measurements obtained at particular gantry rotation angles. A group of projection data sets form a complete scan of object 22. A reconstruction module 34 receives sampled and digitized x-ray data from DAS 32 and performs high speed reconstruction as explained below. The reconstruction data sets output by the reconstruction module 34 are applied as an input to a computer module 36 which stores the reconstruction data sets in memory 38. The reconstruction data sets may represent volumetric data sets and/or image slices through the object 22. Computer 36 also receives commands and scanning parameters from an operator via console 40 that has a keyboard. An associated cathode ray tube display 42 allows the operator to observe reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position object 22 in gantry 12. Particularly, table 46 moves portions of object 22 through gantry opening 48.

EKG leads 17 are joined to the object 22 to detect cardiac activity. The leads 17 generate EKG signals that are digitized, processed, filtered and the like, by the EKG processor module 21. The EKG processor module 21 provides the EKG signals to the computer module 36 and/or to the reconstruction module 34. Alternatively, the EKG processor module 21 may process the EKG signals and output to the computer or reconstruction modules 36 or 34 time stamps associated with particular points in the cardiac cycle. The computer module 36 or reconstruction module 34 associates of the time stamps or EKG signals with corresponding projection data sets to identify the cardiac activity at the time, at which an associated projection data set is obtain. Alternatively, one of the reconstruction module 34 and the computer module 36 may generate, based on the EKG signal, a time stamp. The time stamps identify a unique point in the cardiac cycle (e.g. the R-wave, the P-wave, X milliseconds following the R-wave and the like). The computer module 36 or reconstruction module 34 stores the time stamp with, or uniquely correlates the time stamp to, a corresponding projection data set. Thus, each projection data set is associated with a particular table position and gantry rotation angle, as well as a particular point in the cardiac cycle, at which the projection data set was acquired. Each time stamp and corresponding projection data set are stored in memory 38. The memory 38 stores a group of projection data sets for a complete scan or examination of object 22. The group of projection data sets correspond to a volumetric area of the object 22.

The reconstruction module 34 accesses, at least twice, the group of the projection data sets obtained during a single scanning operation of a volumetric area. The reconstruction module 34 accesses a common group of projection data sets first during a EKG gated reconstruction and again during a non-gated reconstruction. The gated and non-gated reconstruction by the reconstruction module 34 do not operate upon separate or independent scans or examinations of the object 22. In the EKG gated reconstruction, a subset of projection data sets is used, namely only projection data sets obtained at a particular time in the cardiac cycle, or obtained within a limited range of times, within the cardiac cycle. For example, the EKG gated reconstruction may be based on projection data sets only obtained at the peak of the R-wave, or at X msec following the peak of the R-wave.

The reconstruction module 34 performs the non-gated reconstruction utilizing a portion of all or substantially all of the projection data sets obtained during the scan, independent of the time stamp or time at which the projection data set was obtained in the cardiac cycle. The reconstruction module 34 stores gated and non-gated reconstruction data in memory 38. The reconstruction module 34 then combines at least portions of the EKG gated reconstruction data and the non-gated reconstruction data to form combined reconstruction data for the scan or examination. The combined reconstruction data contains a central region, corresponding to the location of the heart that is corrected for motion artifacts. The combined reconstruction data contains a peripheral region corresponding to the area surrounding the heart that is based on actual attenuation measurements from a region of the detector having active detector elements that extend across the full field of view (FOV).

For some types of examinations, interest is first directed to a region of interest (ROI) within an object 22. When object 22 is a patient and ROI is a relatively small organ of interest (OOI), it is desirable to limit patient dose outside the OOI. Projection readings outside the OOI are useful for tomographic reconstruction. It has been found that these readings need not be highly accurate in order to produce excellent images inside the OOI using a fast magnitude decay reconstruction filter kernel. Projections of a multi-slice scanner do not change quickly from row to row because human anatomy does not change much over several millimeters along a patient's axis. Therefore, in one embodiment, projection information collected on one of the rows is used to estimate projection values on other rows outside the OOI. The patient is irradiated fully for all rows for the region inside the OOI. For the region inside the OOI, only a small portion of the entire detector is exposed to x-rays.

Figure 3:
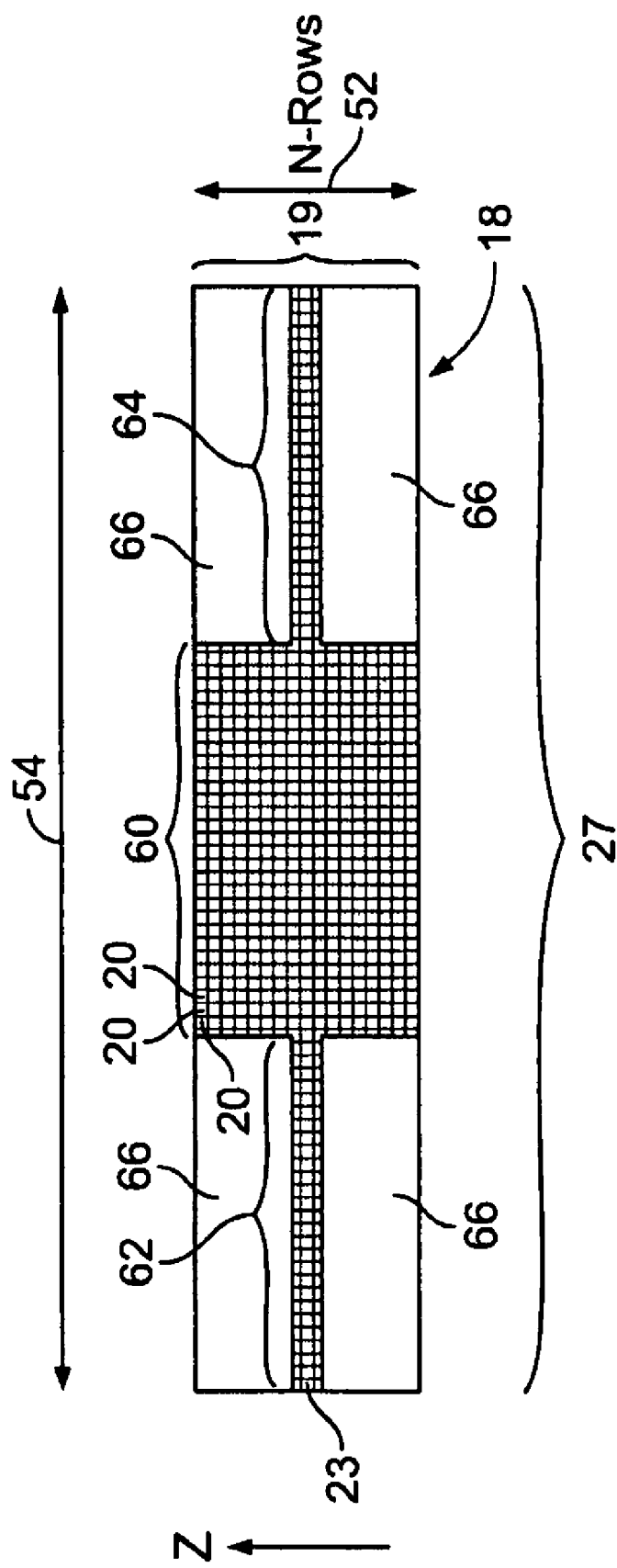
FIG. 3 illustrates a detector configured in accordance with an embodiment of the present invention.

FIG. 3 illustrates a configuration for a detector 18 formed in accordance with an embodiment of the present invention. The detector 18 is comprised of an array of detector elements 20 that are arranged in a non-uniform cross-section in the Z-direction. The curvature of detector 18 is not shown in FIG. 3. The detector 18 is held and oriented in the gantry 12 such that the detector 18 rotates in the XY-direction, while object 22 is moved past the detector 18 in the Z-direction. The detector 18 is shaped to have a width 52 and a length 54, with N-rows 19 of detector elements 20, each row 19 extending at least partially along the length 54. The detector 18 is divided along the length 54 into a central region 60 located between outer regions 62 and 64. Each of the central and outer regions 60, 62 and 64 include at least one common row 23 of detector elements 20, while the central region 60 includes more rows 19 of detector elements 20 than in outer regions 62 and 64. In the example of FIG. 3, the detector elements 20 are configured in a "Chevy" shape, where the central region 60 has more rows 19 of detector elements 20 in the Z-direction than the number of rows 19 in outer regions 62 and 64. Within the central region 60, there are fewer detector elements 20 in each row 19, as compared to the rows 19 that extend through the central and outer regions 60, 62 and 64.

The outer regions 62 and 64 include blocked regions 66 that may have no detector elements 20. Alternatively, blocked regions 66 may include inactive or insensitive detector elements 20 or detector elements 20 that are covered with an x-ray collimator or blocking material. As an example, the outer regions 62 and 64 may have only a single or two rows 23 of active detector elements 20 extending along the full field of view (FOV) of the detector 18. The full FOV corresponds to the full length 54 of the detector 18. Alternatively, the outer regions 62 and 64 may have more than a single row 19 of active detector elements 20, but fewer rows 19 of active detector elements 20 than in the central regions 60. In the example of FIG. 3, the active detector elements 20 in the outer regions 62 and 64 are centered relative to the width 52 of the detector 18. Each of outer regions 62 and 64, have a pair of blocked regions 66 bordering opposite sides of the active detector elements 20.

Optionally, the detector 18 may be configured with other shapes and arrangements of active the detector elements 20 such that one or more of the central, outer and blocked regions 60, 62, 64 and 66 have thicknesses and/or shapes that differ from the exemplary embodiments shown and described herein. In operation, when object 22 is scanned, the detector 18 generates separate projection data sets at select gantry rotational angles, with each projection data set including a set of attenuation measurements for the active detector elements 20 of the detector 18 while positioned at the corresponding select gantry rotational angle. Projection data sets are collected from the detector 18 at multiple discrete views or gantry angles. A group of the projection data sets, corresponding to different views about the object 22, is obtained while the detector 18 rotates about the object 22 and the object 22 moves in the Z-direction. Optionally, the scan may represent a spiral or helical scan, in which the object 22 is moved through the detector 180 in the Z-direction while the detector 18 obtains the group of projection data sets associated with an examination or scan of a volumetric area.

In one exemplary embodiment, detector 18 is an eight-slice detector having eight rows 19 (not shown in FIG. 3). Outer regions 62 and 64 are each two detector rows 19 thick in the Z-direction. In another exemplary embodiment, regions 62 and 64 are less than one detector row 19 thick in the Z-direction. Other embodiments have collimated radiation beams that produce regions 60, 62, and 64 having thicknesses and/or shapes different from those shown and described.

Figure 4:
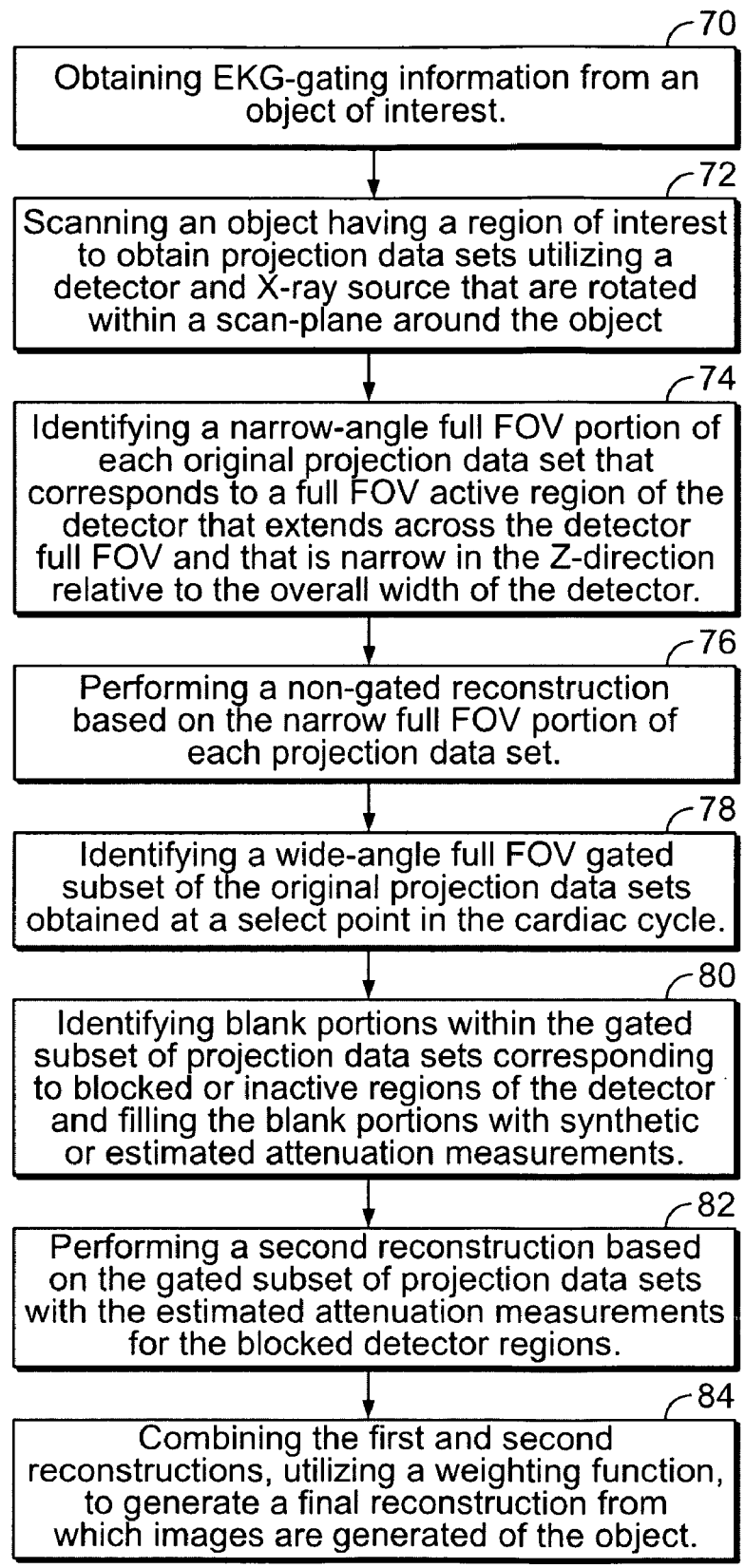
FIG. 4 illustrates a flow chart setting forth the reconstruction process carried out in accordance with an embodiment of the present invention.

FIG. 4 illustrates a flow chart setting forth an exemplary process carried out by the reconstruction module 34 when performing gated and non-gated reconstructions based on at least a partially common group of projection data sets. Beginning at 70, EKG leads 17 attached to the object 22 monitor the cardiac cycle of a patient. EKG signals from leads 17 are supplied to the EKG processor module 21 which produces EKG gating information for the object 22. Simultaneously, while EKG gating information is being obtained at 70, the scanning operation is performed at 72. At 72, in order to perform a complete scanning operation of a volume of interest, the x-ray source 14 and a detector 18 rotate about an object 22. The object may be moved in the Z-direction continuously or intermittently through a desired range of motion. As the x-ray source 14 and detector 18 rotate, projection data sets are collected through the DAS 32 at select times at various gantry rotation angles.

Optionally, projection data sets may be obtained by the DAS 32 based on a system clock or at uniform intervals/ rotation angles about the gantry 12. Alternatively, the projection data sets may be obtained in a manner synchronized to the EKG signal and the gating information. For example, the computer module 36 may direct the DAS 32 to collect projection data sets only at select points during the cardiac cycle, where the computer module 36 determines the select points in the cardiac cycle based on EKG signals provided from the EKG processor module 21. The scanning operation is continued at 72 and EKG gating information is continuously collected at 70 until a complete examination or full scan of a volume of interest is obtained. The object 22 may remain stationary throughout the entire scan or may move intermittently or continuously. The group of projection data sets collected during the examination or full scan are stored in the memory 38.

At 74, the reconstruction module 34 identifies a narrow angle full field of view (FOV) portion of each original projection data set. The narrow angle is measured in the Z-direction and thus only corresponds to the full FOV active rows (e.g., rows 23 in the example of FIG. 3). The term "narrow angle" is used to distinguish from the complete width 52 of the detector 18. The term "full field of view" refers to the full length 54 of the detector 18. Active rows 23 extend along a full field of view 27 in the example of FIG. 3.

At 76, once the narrow, angle full field of view portions of each original projection data set have been identified, a non-gated reconstruction is performed by the reconstruction module 34 based thereon and stores a non-gated reconstruction data set or volume in memory 38. The non-gated reconstruction is performed based on each and every projection data set during the examination, independent of the time stamp or gating information. Alternatively, the non-gated reconstruction, at 76, may be performed based on a non-gated sub-set of the projection data sets, for example, for the projection data sets extending along a portion of the Z-direction (e.g., a 5, 10, 15 centimeter long region).

At 78, the reconstruction module 34 identifies a wide angle full FOV sub-set of the projection data sets that were each obtained at the same time in the cardiac cycle. This determination is based on the time stamps stored with each projection data set. For example, the projection data sets only acquired at the peak of the R-wave may be identified at 78 to collect a gated sub-set of projection data sets. The wide angle is measured in the Z-direction and equals the width 52.

At 80, the reconstruction module 34 identifies the blank portions of the projection data sets corresponding to the blocked regions 66 on the detector 18. The reconstruction module 34 fills-in missing attenuation measurements for the blank portions of the projection data set corresponding to the blocked regions 66. The reconstruction module 34 fills in the missing attenuation measurements with estimated attenuation measurements. By way of example, with reference to FIG. 3, the estimated attenuation measurements for each of the blocked regions 66 in the outer regions 62 is copied from the attenuation measurements detected by active detector elements 20 in the rows 23 of the outer region 62. Similarly, the reconstruction module 34 fills-in missing attenuation measurements associated with the blocked regions 66 in the outer region 64 by also copying attenuation measurements from detector elements 20 in the outer regions 64. The copied attenuation measurements are reproduced for each position associated with a synthetic or blocked detector element in the blocked regions 66 of the outer regions 64. Alternative estimation processes may be utilized to fill-in the estimates of attenuation measurements for the blocked regions 66. The reconstruction module 34 performs the foregoing operation for each projection data set in the wide angle full FOV gated sub-set of the projection data sets identified at 78.

At 80, the reconstruction module 34 fills-in missing attenuation measurements within the gated sub-set of projection data sets. The missing attenuation measurements are located in the portion of the projection data sets that corresponds to the positions of the blocked region 66. Once the missing attenuation measurements are filled-in, the resulting data sets represent a gated sub-set of projection data sets, each of which partially contains actual attenuation measurements and partially contains estimated attenuation measurements.

At 82, the reconstruction module 34 performs a gated reconstruction based on the gated sub-set of projection data sets. The gated reconstruction utilizes, from the gated sub-set of projection data sets, actual attenuation measurements from the active detector elements 20, as well as the estimated attenuation measurements synthetically created to fill in the blocked regions 66 The gated reconstruction utilizes projection data sets from the full field of view 27 of the detector 18 and from the full width 52 (e.g., from 64 rows or slices of detector elements 20. The reconstruction module 34 stores the resulting gated reconstruction data volume in memory 38 as a gated reconstruction data set or volume.

At 84, the reconstruction module 34 combined the gated and non-gated reconstruction data sets based on a weighting function to generate a final reconstruction data set of an object. Images may be generated by the reconstruction module 34 or by the computer module 36 based on the final reconstruction data set.

Considering one exemplary embodiment in detail, let $P(\gamma, k)$ denote projection data detected by detector 18 during a scan with detector angle $\gamma$ and detector row k. Only the nth detector row of detector rows 23 is fully exposed to x-rays for the entire projection. Denoting a detector angle that corresponds to a boundary of the OOI by $\gamma_0$, the entire OOI region is denoted by $(\gamma_0, \gamma_0)$. An angular extent of a first region is limited to substantially an angle subtended by the OOI, and a second region has an angular extent at least equal to that of detector 18.

Object 22 is scanned with imaging system 10, and attenuation measurements are collected by detector 18. Projection data for detector row k ($k \neq n$) is determined by an equation written:

$$P(\gamma, k) = \begin{cases} P(\gamma, k) & -\gamma_0 + \delta \leq \gamma \leq \gamma_0 - \delta \\ \theta(\gamma)P(\gamma, k) + [1 - \theta(\gamma)]P(\gamma, n) & \text{otherwise.} \end{cases}$$

where:

$$\theta(\gamma) = 3w^2(\gamma) - 2w^3(\gamma),$$

$$w(\gamma) = \begin{cases} \dfrac{\gamma + \gamma_0}{\delta} & -\gamma_0 \leq \gamma < -\gamma_0 + \delta \\ 1 & -\gamma_0 + \delta \leq \gamma < \gamma_0 - \delta \\ \dfrac{\gamma_0 - \gamma}{\delta} & \gamma_0 - \delta \leq \gamma < \gamma_0 \\ 0 & \text{otherwise,} \end{cases}$$

and δ is a parameter that defines a width of a transition region. The above equation uses projection data for one row n to replace projection data for other rows outside of the OOI. The "feathering" or "blending" that takes place removes discontinuities encountered during projection substitution. In other embodiments, other techniques may be used to blend the two signals together. Based on the above equation, projections outside the OOI for detector rows other than n are given a weighting function of zero. Therefore, these projection samples are not contributing to the final reconstructed images. In one embodiment, these projection samples are omitted from data collection.

Attenuation measurements from a penumbra of radiation beam 16 provide some information that can be used for imaging an object 22. It is desirable to make use of all of the information collected. Therefore, in one embodiment, data from all detector rows are summed (after a logarithm operation) and the sum is used as a basis for projection estimation outside the OOI.

The above techniques and apparatus realize significant patient x-ray dose reduction. For example, in a cardiac study, a majority of a patient's heart can easily be fitted inside a 25 cm field of view (FOV). For a 50 cm FOV scanner, a scan of the patient's heart utilizes about 58% of the detector cells. For an eight-slice scanner, if only one detector row outside the OOI is selected for exposure (in fact, only exposure of a fraction of a detector row is needed), the additional exposed x-ray region is only 5% of an entire detector channel. Therefore, the overall dose saving is roughly 1.00−0.58−0.05=0.37, or 37% in an embodiment in which region 58 has an angular extent essentially coextensive with the 25 cm FOV.

To verify certain of the above, methods and apparatus, a shoulder phantom was scanned in a helical scan mode having a 3:1 pitch. A shoulder phantom was selected as being representative of a "worst case" condition, because the densest bones are outside a center region for which reconstruction was to be attempted. For this experiment, δ was to be 20 channels wide. Projections for all rows (except one row adjacent a center of the detector) were truncated outside a 30 cm FOV. Equation 1 was then applied to produce all projections. An image was then reconstructed. Two other images were produced for comparison, one utilizing the entire FOV for the CT imaging system (54.7° for this system) and one utilizing the 30 cm FOV, but without truncation. Visually, no image difference was observed between the truncated image to which equation 1 was applied and the other two images. A difference image of the 30 cm FOV was produced from an image utilizing the entire FOV of the imaging system and the truncated image. This difference image showed no visible structures.

In embodiments described above, the detector 18 was collimated so that region 60 was symmetrical with respect to an isocenter 24 (FIG. 2), i.e., the region selected was $-\gamma_0 < \gamma < \gamma_0$. In another embodiment, the detector 18 may be collimated asymmetrically, so that fully scanned region 60 is asymmetric. For example, the first beam is collimated as $-\gamma_1 < \gamma < \gamma_0$, where $\gamma_1 \neq \gamma_1$. An advantage of this approach is that it minimizes the impact of a transition region, because the two boundaries are not aligned.

In another embodiment, the detector 18 is collimated to fully or partially block only one outer region 62 or 64, but not both. For example, scans of at least 360° may collect projection data from outer region 62, which is used in image reconstruction to fill in information from the blocked outer region 64.

In yet another embodiment, a single-slice scanner may be used in which a thicker region of an ROI is scanned than regions outside the ROI. In one embodiment and referring again to FIG. 3, detector 18 would have only one detector row in the Z-axis direction. Beam 16 (FIG. 2) is collimated to have a thicker, first region and a thinner, second region. During a scan, ROI is scanned in thicker, first region. In another embodiment, a plurality of scans are performed to acquire projection data for reconstructing a plurality of images of image of ROI, with table 46 indexed between scans. However, some of the plurality of scans are performed with a radiation beam collimated to have a reduced angular extent. The reduced angular extent is, for example, coextensive with ROI. Data acquired during one or more scans using a full angle of the radiation beam are used to supply missing information in the scans performed using a reduced angular extent of the radiation beam.

In the above examples, the EKG signal was used to gate the cardiac acquisition. Alternatively, other gating methods may be used to monitor the phase of the heart and provide guidance for data acquisition. For example, contrast uptake can be used as the gating instead of the EKG signal. In the above examples, cardiac imaging has been used as an example. Other organs may also be imaged in a similar fashion. For example, the liver region may be imaged by centering the inner ROI of the detector with the liver and using the outside region to estimate the outer bodies.

Figure 5:
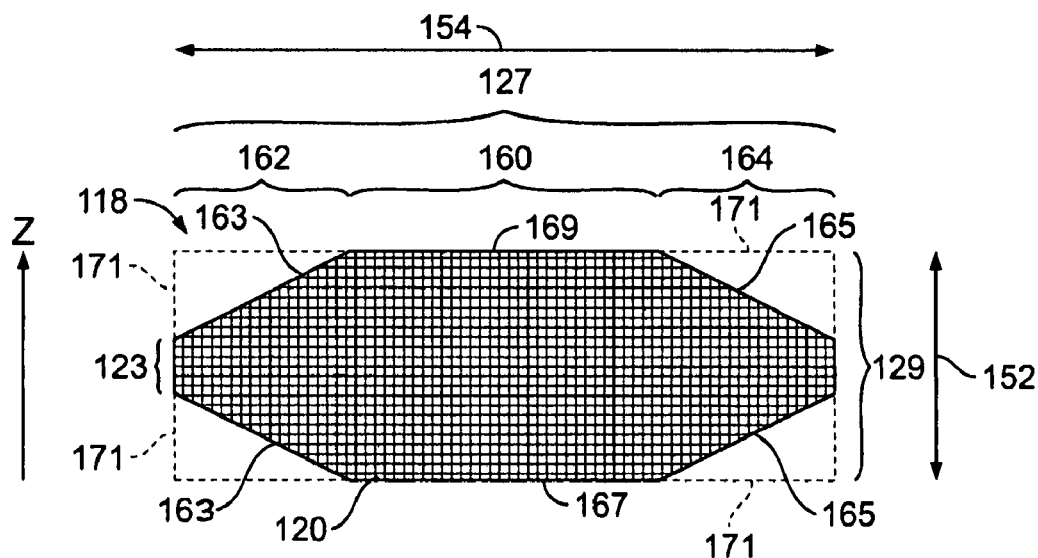
FIG. 5 illustrates a detector configured in accordance with an alternative embodiment of the present invention.

FIG. 5 illustrates a detector 118 formed in accordance with an alternative embodiment of the present invention. The detector 118 is configured to collect projection data sets as an object is moved in the Z-direction. The detector 118 has a length 154 extending transverse to the Z-direction and a width 152 extending parallel to the Z-direction. The length 154 defines the full field of view 127, while the width 152 defines the widest angle 129 in the Z-direction over which the detector 118 is able to collect projection data sets. The detector 118 has an overall trapezoidal shape and includes a central region 160 border on opposite ends by outer regions 162 and 164. The central region 160 has active detector elements extending along the widest angle 129 in the Z-direction. The detector 118 is comprised entirely of active detector elements 120, with no inactive detector elements. The outer regions 162 and 164 are generally triangularly shaped with opposite tapered side edges 163 and 165 that extend toward one another from the front and rear edges 167 and 169 of the central region 160.

During a gated reconstruction, the reconstruction module 34 fills in estimated or synthetic attenuation measurements for the areas denoted by dashed lines 171. The estimated attenuation measurements are generated based on actual attenuation measurements collected by the active detector elements 120 in the outer regions 162 and 164. During a non-gated reconstruction, the reconstruction module 34 utilizes attenuation measurements collected by the active detector elements 120 in the rows 123 extending along the full field of view 127. The detector rows 123 are narrow in the Z-direction relative to the overall width 152 of the detector 118.

Figure 6:
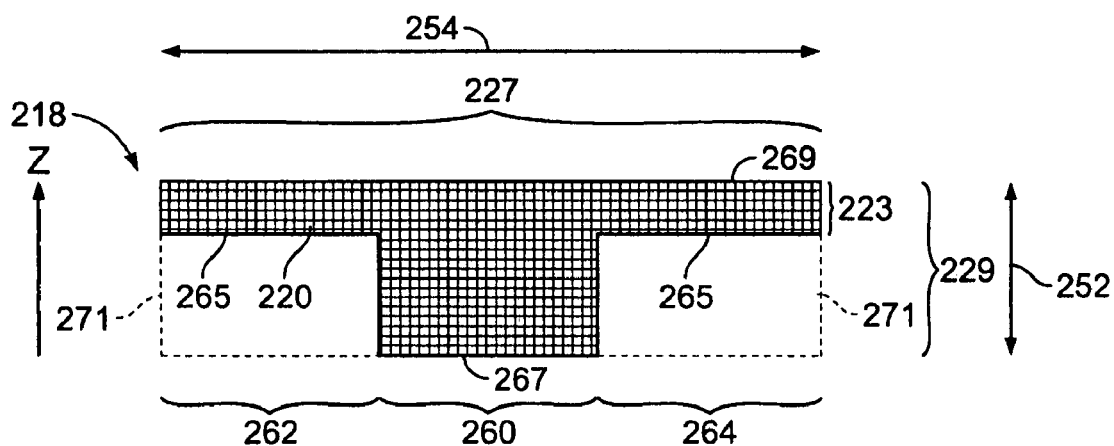
FIG. 6 illustrates a detector configured in accordance with an alternative embodiment of the present invention.

FIG. 6 illustrates a detector 218 formed in accordance with an embodiment of the present invention. The detector 218 has a length 254 and a width 252. The length 254 extend along the full field of view 227, while the width 252 defines the widest angle 229 in the Z-direction. The detector 218 includes a central region 260 bordered by outer regions 262 and 264. The detector 218 is generally T-shaped with a common edge 269 extending along each of the central and outer regions 260, 262 and 264. The outer regions 262 and 264 have edges 265 that extend in-line with one another and extend parallel to, but are arranged in a stepped manner, with the edge 267 of the central region 260.

During a gated reconstruction, the reconstruction module 34 fills in estimated or synthetic attenuation measurements for the areas denoted by dashed lines 271. The estimated attenuation measurements are generated based on actual attenuation measurements collected by the active detector elements 220 in the outer regions 262 and 264. During a non-gated reconstruction, the reconstruction module 34 utilizes attenuation measurements collected by the active detector elements 220 in the rows 223 extending along the full field of view 227. The detector rows 223 are narrow in the Z-direction relative to the overall width 252 of the detector 218.

Figure 7:
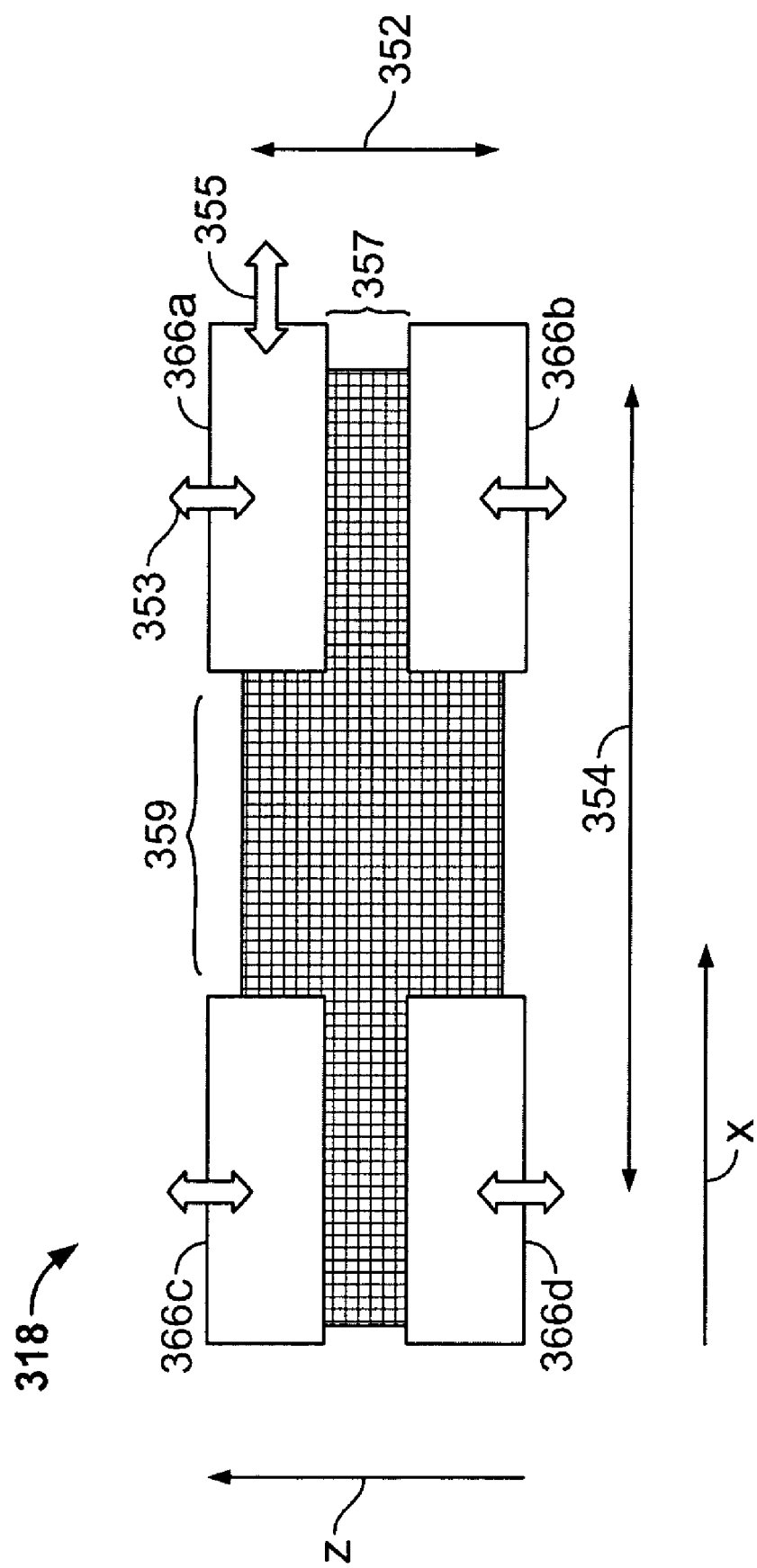
FIG. 7 illustrates a detector configured in accordance with an alternative embodiment of the present invention.

FIG. 7 illustrates a detector 318 formed in accordance with another embodiment. The detector 318 has a width 352 and length 354, both of which are adjustable parallel to the Z-direction and to the X-direction by moving pre-patient collimation inward and outward in the direction of arrows 353 and 355. The outer regions 366a-366d represent areas of the detector 318 that are blocked by pre-patient or post-patient collimation. As one example, the outer regions 366a-366d may constitute collimators.

Outer regions 366a and 366b are separate by an exposure area width 357. Outer regions 366c and 366d are also separated by the exposure area width 357. Outer regions 366a and 366c are separated by a central exposure area 359. Outer regions 366b and 366d are also separated by the central exposure area 359. The size of the exposure area width 357 and central exposure are 359 is adjustable by moving the pre- or post-patient collimation. Optionally, the location of the exposure area width 357 relative to the detector 318 may be shifted parallel to the Z-direction, by shifting all of the outer regions 366a-366d in the same direction. Optionally, the location of the central exposure area 359 relative to the detector 318 may be shifted parallel to the X-direction, by shifting all of the outer regions 366a-366d in the same direction.

Based on the patient heart rate, the helical pitch may be adjusted to ensure complete coverage of the entire heart. As the helical pitch increases, the exposure area width 357 of the detector 318 (shown in FIG. 7) is widened. This may be accomplished by shifting the collimators outward to open up the exposure area width 357. For slower helical pitch, the exposure area width 357 can be narrower. In addition, the collimation may be adjusted horizontally in the direction of arrows 355 so that the central exposure area 359 may be adjusted to different heart sizes and to provide patient centering to minimize the dose to patient. In many cases, the patient heart is not centered. The simplest approach is to open up the central exposure area 359 so that the heart is always in the center FOV of the detector 318. To reduce the dose to patient, the collimation can be adjusted dynamically (shifting left and right) so that the central exposure area 359 may be reduced while the entire heart remains located inside the FOV. Hence, outer portions 366a-366d may all be shifted in one direction along horizontal arrow 355 (e.g., left or right). X-ray dose to patient may be further reduced by combining the above approach with the tube current modulation, and conventional helical reconstruction, when the entire chest or body is imaged. In conventional helical reconstruction, nearly all the projection samples that pass through a particular location will be used to produce the image at that location. In cardiac gated reconstruction, only a partial scan dataset is used. The tube current may be reduced for the regions in which the conventional helical reconstruction takes place.

With recent multi-slice CT scanners, a helical pitch of approximately 0.2:1 is used for cardiac imaging. Even with this low pitch, the entire chest, including the heart, can now be acquired in one patient breath hold with a single helical scan with 32 or 64 or higher multi-slice CT scanner. This is advantageous as one contiguous dataset may be acquired in the minimal amount of time with full utilization of the contrast bolus that was injected into the patient. The drawback, however, is that the low helical pitch results in a large X-ray dose penalty in the chest regions above and below the heart where cardiac gating is not required.

In a typical clinical scenario, 12-15 cm of Z coverage is required to image the heart, whereas approximately 30 cm is necessary to cover the entire chest. Thus, 15-18 cm of the imaged range does not require cardiac gating, but given the low pitch (~0.2:1) helical acquisition, this region is "overscanned" 5 times given the amount of overlap in Z. This results in five times the dose in these regions with respect to a 1:1 pitch helical scan typical of a non-gated imaging mode.

To address this issue, a reconstruction algorithm is designed which takes advantage of the 5× data redundancy due to the helical overlap. If only a 20% of the X-ray dose is applied in the regions above and below the heart (while maintaining a full technique within the heart region), the reconstruction algorithm buys back the signal-to-noise by exploited this redundant data. With the example coverage given above, this mA modulation approach results in an overall dose that is only 52% to 60% that of the full dose chest acquisition.

Figure 8:
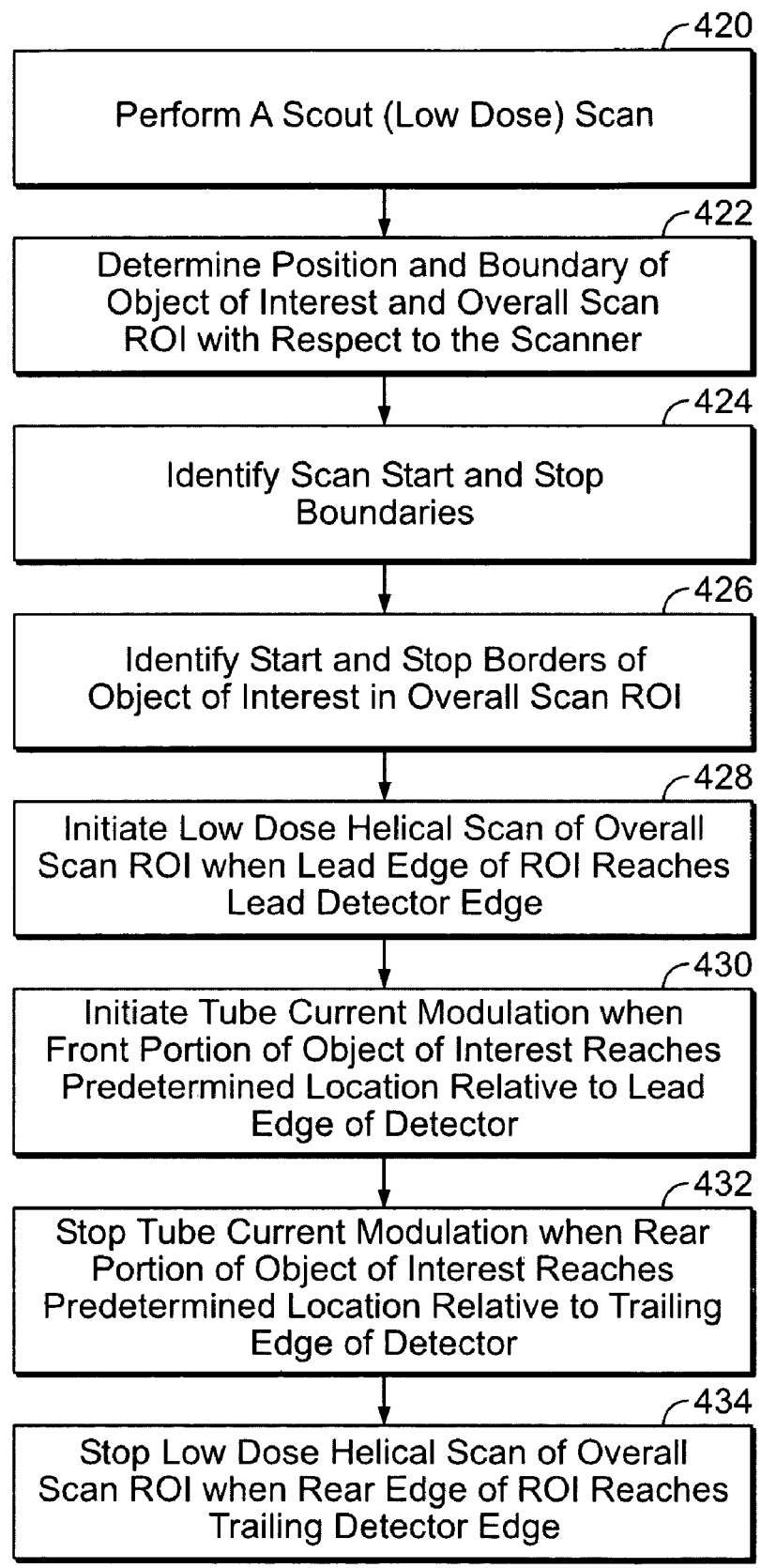
FIG. 8 illustrates a process carried out in accordance with an embodiment of the present invention for tube current modulation.

FIG. 8 illustrates a processing sequence carried out in accordance with scanning an ROI through the use of tube current modulation. The tube current modulation processes described herein need not necessarily use detectors having the shapes illustrated in FIGS. 3 or 5-7. It should be understood that the embodiments and processes described in connection with FIGS. 8 and 9, and described more generally in connection with tube current modulation may be utilized with a conventional detector having multiple rows of detector elements arranged in a conventional rectangular shape (e.g., 2 rows, 8 rows, 32, rows, 64 rows, 256 rows, etc.).

In FIG. 8, at 420, a scout or very low tube current scan is performed by advancing the patient 22 through the CT system 10 while taking very low tube current scans. At 422, the system analyzes the results of the scout scan and determines the position and boundaries of the ROI, as well as the position and boundaries of the object of interest (OOI) within the ROI. The OOI may represent the heart, liver, kidneys, intestines, brain, lateral limb and the like. The position information may correspond to an XYZ coordinate within an XYZ reference coordinate system. A position of the table 46 is known at all times relative to the XYZ reference coordinate system. The table 46 advances the patient 22 along known coordinates within the XYZ reference coordinate system. The boundaries of the object of interest and the ROI may represent points along the Z-axis or a uniform or non-uniform contour surrounding the object of interest and/or the ROI.

At 424, the system identifies start and stop boundaries for the overall scan (e.g. points along the z-axis). At 426, the system identifies start and stop boundaries of the object of interest (e.g. the heart) and the overall scan ROI. At 428, the system initiates a low tube current helical scan of the overall scan ROI. The table 46 is advanced at a predetermined speed along the Z-axis, which corresponds to a desired pitch. The detector 18 includes multiple rows of detector elements (formed in a uniform shape or a non-uniform shape). The pitch may be set to provide a relatively slow scan rate such that different portions of the detector 18 are aligned with a common anatomy of the patient 22 during successive rotations of the detector 18. For example, a leading group of rows of the detector 18 may rotate about a common anatomy during a first scan, while a trailing group of rows of the detector 18 rotate about the common anatomy during a second scan. By controlling the pitch, the detector 18 is able to obtain overlapping sets of scan data regarding a common anatomy.

The tube current (or mA) associated with the scan started at 426 is sufficient to provide at least a certain level of diagnostic information regarding the object, where as the scout scan is at such a low tube current that very little (if any) diagnostic quality information is obtained regarding the object. The low tube current diagnostic helical scan is initiated when the lead edge of the ROI reaches the leading edge of the detector. Alternatively, the low tube current helical scan may be initiated at some earlier or later point, such as a predetermined distance/time before or after the lead edge of the ROI reaches the lead edge of the detector 18.

At 430, the system changes the control power to the x-ray source 14 from a low tube current level to a high tube current level. The high tube current is initiated when the front portion of the object of interest reaches a predetermined location relative to the lead edge of the detector 18. Alternatively, high tube current may be initiated a predetermined time before or after the front edge of the object of interest reaches the lead edge of the detector 18. At 432, the system stops the high tube current when the rear portion of the object of interest reaches a predetermined location relative to the trailing edge of the detector (e.g., the rear boundary of the OOI leaves the rear edge of the detector). Alternatively, high tube current may be stopped a predetermined time before or after the rear edge (or the center) of the object of interest reaches the trailing edge of the detector 18. When the system stops high tube current, the control current to the detector 18 switches back to the low tube current level associated with the helical scan of the overall scan ROI. At 434, the system completes the helical scan of the overall scan ROI when the rear edge of the ROI reaches the trailing detector edge.

Optionally, while scanning the object of interest at 430, the x-ray controller 28 may also modulate the high tube current between first and second levels based on a physiologic parameter that periodically varies. For example, the x-ray controller 28 may alternate the high tube current between first and second levels based on the ECG cycle (e.g., 500 mA at diastole and 200 mA at systole). As a further option, while scanning the ROI (at 428 and 432) before and after the object of interest, the X-ray controller 28 may also modulate the low tube current between first and second levels based on a physiologic parameter that periodically varies. For example, the x-ray controller 28 may alternate the low tube current between first and second levels based on the ECG cycle (e.g., 100 mA at diastole and 20 mA at systole).

Figure 9A:
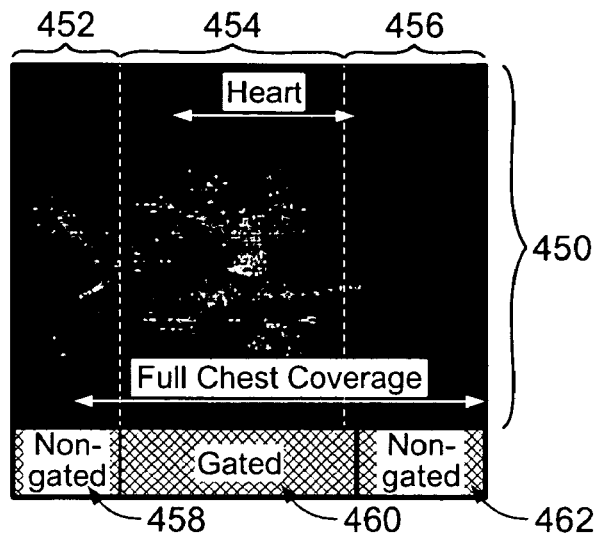
FIG. 9 illustrates a pictorial representation of controlling tube current modulation relative to an object of interest.

FIG. 9A illustrates a pictorial representation of the manner in which tube current may be controlled between high and low levels (see vertical axis labeled Tube Current) as an object of interest advances through the CT system 10 over time (see horizontal axis labeled time). A scan area 450 is shown to be divided into a leading portion 452, an OOI portion 454 and a trailing portion 456. In the example of FIG. 9A the scan area 450 is also apportioned into a leading non-gated area 558, a gated area 460 and a trailing non-gated area 462. Projection data sets obtained from the leading and trailing non-gated areas 458 and 462, when utilized during reconstruction, are not organized or selected based on ECG gating information. Projection data sets obtained form the gated area 460, when utilized during reconstruction, may be organized or selected based on ECG gating information.

Figure 9B:
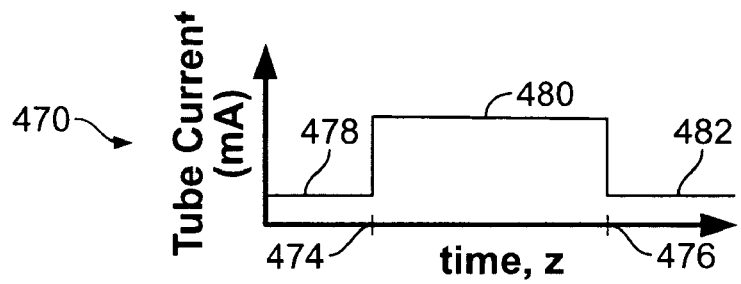
Figure 9C:
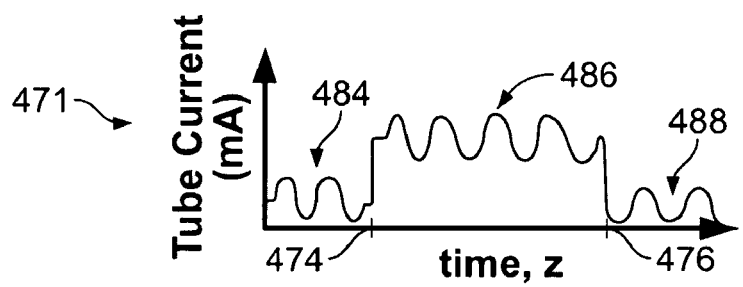
Figure 9D:
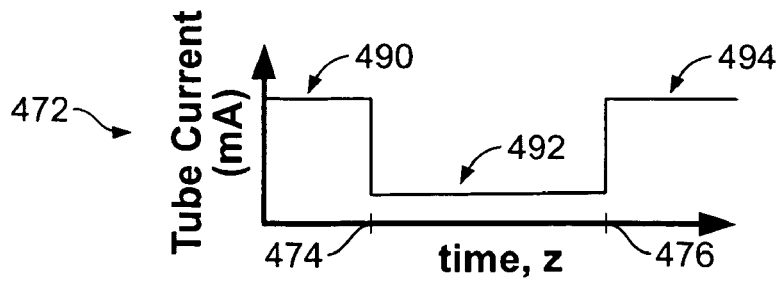

FIGS. 9B-9D also illustrate exemplary, alternatively tube current modulation patterns 470-472 that may be used to control the x-ray source 14 during a an overall ROI scan. Each modulation pattern 470-472 shows the tube current in mA over time. Points 474 and 476 correspond to Z-coordinates of the leading and trailing edge of the organ of interest within the ROI. Alternatively, points 474 and 476 may represent Z-coordinates having some other relation to the organ of interest (e.g., X inches from the center of the organ of interest, X inches from a select feature of the organ of interest). In the first pattern 470, the tube current is initially set at a low current level 478 and maintained at a steady state until reaching point 474. At point 474, the tube current is increased to a high current level 480 and maintained at a steady state until reaching point 476. At point 476, the tube current is again decreased to the low current 482 steady state for the remainder of the scan.

In the second pattern 471, the tube current is initially set at a low current level 484 and modulated (e.g., 20 to 100 mA) based on a physiologic parameter (e.g., the cardiac cycle or breathing) until reaching point 474. At point 474, the tube current is increased to a high current level 486 and again modulated (e.g., 300 to 500) based on a physiologic parameter until reaching point 476. At popint 476, the tube current is again decreased to the low current 488 and modulated (e.g., 20 to 100 mA) for the remainder of the scan. Optionally, the low current level 484 and 488 may be constant, while the high current level 486 may be modulated.

In the third pattern 472, the tube current is initially set at a high current level 490 and maintained at a steady state until reaching point 474. At point 474 the tube current is decreased to a low current level 492 and maintained at a steady state until reaching point 476. At point 476, the tube current is again increased to the high current 494 steady state for the remainder of the scan.

Figure 10:
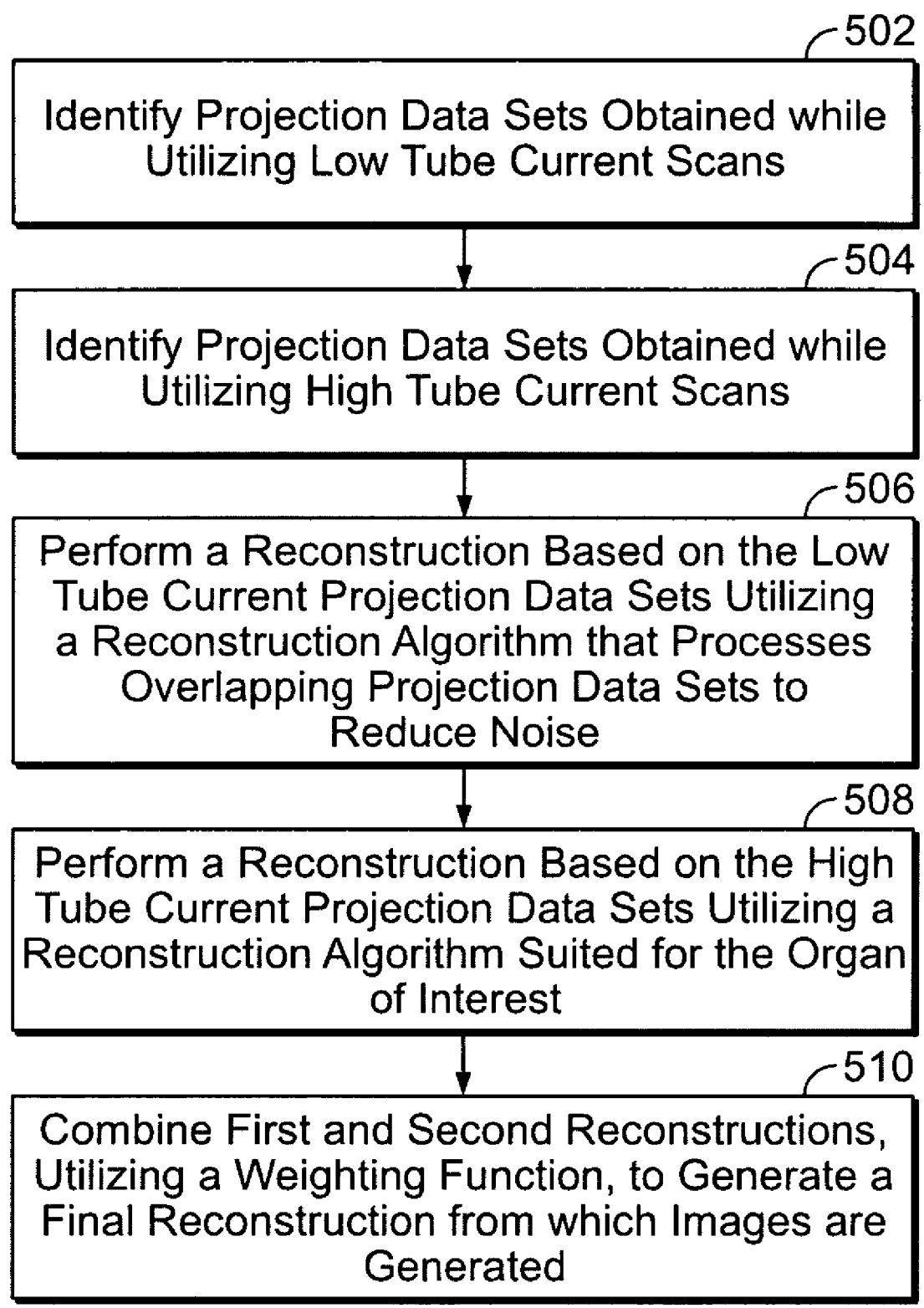
FIG. 10 illustrates a process carried out in accordance with an embodiment of the present invention for performing reconstruction based on projection data sets obtained during tube current modulation.

FIG. 10 illustrates the processing sequence carried out to perform reconstruction upon the projection data sets obtained during tube current modulation. At 502, the reconstruction module 34 (FIG. 1) identifies a first group of projection data sets that were obtained during low tube current scans. In the examples of pattern 470 and 471, the first group would include the projection data sets obtained at current levels 478, 482, 484 and 488. In pattern 472, the first group would correspond to current level 492. At 504, the reconstruction module 34 identifies a second group of projection data sets that were obtained during the high tube current scans. In the examples of pattern 470 and 471, the second group would include the projection data sets obtained at current level 480 and 486. In pattern 472, the second group would correspond to current levels 490 and 494.

At 506, the reconstruction module 34 performs reconstruction based on the low tube current projection data sets. The low tube current projection data sets may have a high content of noise. The reconstruction algorithm corrects for the noise by performing reconstruction based on overlapping projection data sets. By way of example, the system may use the algorithm described in a technical paper entitled "Reconstruction-plane-dependent weighted FDK algorithm for cone beam volumetric CT", by Xiangyang Tang and Jiang Hsieh, Applied Science Laboratory, GE Healthcare Technologies, Waukesha, Wis., the complete subject matter of which is expressly incorporated by reference in its entirety. The reconstruction at 506 products a low current reconstruction data set.

At 508, the reconstruction module 34 performs reconstruction based on the high tube current projection data sets. The high tube current projection data sets have low noise relative to the low tube current projection data sets. The high tube current projection data sets may be selected based on a physiologic parameter. For example, the high tube current projection data sets may be selected for reconstruction based on ECG gating information when the organ of interest is the heart. In this example, a reconstruction algorithm suited for ECG gated reconstruction may be used (e.g., the algorithm described above in connection with FIG. 4). Alternatively, when the organ of interest is the liver or kidney, the same or another reconstruction algorithm may be used that is tailored to reconstructions of such organs. The reconstruction at 508 products a high current gated reconstruction data set.

At 510, the high and low current reconstruction data sets are combined utilizing a weighting function similar to the weighting function explained above in connection with FIG. 4. The combined data sets form a final reconstruction data set from which images may be formed.

While the invention has been described in terms of various specific embodiments, those skilled in the art will recognize that the invention can be practiced with modification within the spirit and scope of the claims.

What is claimed is:

1. A method for performing computed tomography (CT) imaging, the method comprising:
   obtaining physiologic gating information from an object;
   obtaining attenuation measurements from the object utilizing a detector that is rotated in a scanned plane about the object and that detects x-rays passing through the object;
   performing a first reconstruction of the object based on the attenuation measurements collected by a first narrow angle full field of view region of the detector having selectively activated detector elements to obtain a first reconstruction data set, the first reconstruction being performed independent of the physiologic gating information; and
   performing a second reconstruction of the object based on attenuation measurements collected by a second wide angle full field of view region of the detector having at least some different selectively activated detector elements and based on the physiologic gating information to obtain a second reconstruction data set.

2. The method of claim 1, wherein the detector has a non-uniform cross-section in a Z-direction, the Z-direction representing a direction along which the object is moved through the scanned plane.

3. The method of claim 1, wherein the first and second regions partially differ and partially overlap.

4. The method of claim 1, further comprising adjusting at least one of a width and length of the detector by moving collimation.

5. The method of claim 1, further comprising forming a combined reconstruction data set by combining a central portion of the second reconstruction data set and peripheral portion of the first reconstruction data set.

6. The method of claim 1, further comprising moving the in the Z-direction during scanning, the detector having a length transverse to the Z-object direction and a width in the Z-direction, the length being greater than the width.

7. The method of claim 1, wherein the first and second regions have corresponding different first and second widths along a Z-direction, at least one of the first and second widths being adjustable along the Z-direction based on a pitch at which the detector rotates about the scanned plane.

8. The method of claim 1, wherein the second region collects attenuation measurements from a heart of a patient and the first region collects attenuation measurements from a portion of a patient surrounding the heart.

9. The method of claim 1, wherein the detector has shape that is wide in a Z-direction along a central region and long transverse to the Z-direction in outer regions.

10. The method of claim 1, wherein the physiologic gating information comprises EKG gating information and wherein a central portion of the second reconstruction data set is corrected for motion artifacts based on the EKG gating information, while a central portion of the first reconstruction data set is not corrected for motion artifacts.

11. The method of claim 1, wherein an outer portion of the second reconstruction data set is based on actual attenuation measurements, while an outer portion of the first reconstruction data set is based on estimated attenuation measurements.

12. The method of claim 1, further comprising switching a tube current that drives an x-ray source from a lower level to a higher level when an object of interest in the object is located within the scan plane of the detector.

13. A computed tomography (CT) system, comprising:
   a physiologic input configured to receive physiologic gating information from an object;
   an x-ray source and x-ray detector configured to rotate within a scanned plane around an object, the detector obtaining attenuation measurements from the object as the object is moved in a Z-direction through the scanned plane using a movable member; and
   a reconstruction module performing a first reconstruction of the object based on the attenuation measurements collected by a first narrow angle full field of view region of the detector having selectively activated detector elements and independent of the physiologic gating information to obtain a first reconstruction data set, the reconstruction module performing a second reconstruction of the object based on attenuation measurements collected by a second wide angle full field of view region of the detector having at least some different selectively activated detector elements and based on the physiologic gating information to obtain a second reconstruction data set.

14. The system of claim 13, wherein the detector has a non-uniform cross-section in the Z-direction, along which the patient is moved through the scanned plane.

15. The system of claim 13, wherein the first and second regions partially differ and partially overlap.

16. The system of claim 13, wherein the reconstruction module forms a combined reconstruction data set by combining a central region of the second reconstruction data set and a peripheral region of the first reconstruction data set.

17. The system of claim 13, further comprising collimators adjustable along at least one of a width and length of the detector.

18. The system of claim 13, wherein the first and second regions have corresponding different first and second widths along the Z-direction, at least one of the first and second widths being adjustable along the Z-direction based on a pitch at which the detector rotates about the scanned plane.

19. The system of claim 13, wherein the detector has a shape that is wide in the Z-direction along a central region and long transverse to the Z-direction in outer regions.

20. The system of claim 13, wherein the physiologic gating information comprises EKG gating information and wherein the central portion of the second reconstruction data set is corrected for motion artifacts based on the EKG gating information, while a central portion of the first reconstruction data set is not corrected for motion artifacts.

21. The system of claim 13, wherein an outer portion of the first reconstruction data set is based on estimated attenuation measurements, while an outer portion of the second reconstruction data set is based on actual attenuation measurements, not estimated attenuation measurements.

22. The system of claim 13, further comprising an x-ray controller that switches a tube current that drives the x-ray source from a lower level to a higher level when an object of interest in the object is located within the scan plane of the detector.

23. The system of claim 13, further comprising an x-ray controller that modulates a tube current that drives the x-ray source when an object of interest in the object is located within the scan plane of the detector.

24. The system of claim 13, wherein the physiologic gating information comprises EKG gating information and further comprising an x-ray controller that modulates a tube current that drives the x-ray source in connection with the EKG gating information.

25. The system of claim 13, wherein the x-ray source and x-ray detector perform a scout scan controlled by a controller to identify a boundary an object of interest in the object, the system further comprising an x-ray controller that modulates a tube current that drives the x-ray source based a location of the boundary relative to a position of the detector.

26. The system of claim 13, wherein the physiologic gating information comprises EKG gating information, and further comprising:
   a computer module that identifies first and second regions of the object, the second region being associated with the EKG gating information and the first region being unrelated to the EKG gating information; and
   an x-ray controller that changes a tube current that drives an x-ray tube of the x-ray source to utilize a higher tube current when obtaining attenuation measurements from the second region that is associated with the EKG gating information.

* * * * *